(12) United States Patent
Wan et al.

(10) Patent No.: US 10,226,606 B2
(45) Date of Patent: Mar. 12, 2019

(54) URETERAL STENTS

(71) Applicant: C.R. BARD, INC., Murray Hill, NJ (US)

(72) Inventors: Beatrice Wan, Atlanta, GA (US); Robert H. Orr, III, Covington, GA (US); Richard Reineke, Atlanta, GA (US); Jill Walthall, Atlanta, GA (US); Mitch Loy, Monroe, GA (US)

(73) Assignee: C.R. BARD, INC., Murray Hill, NJ (US)

( * ) Notice: Subject to any disclaimer, the term of this patent is extended or adjusted under 35 U.S.C. 154(b) by 53 days.

(21) Appl. No.: 15/126,081

(22) PCT Filed: Apr. 8, 2015

(86) PCT No.: PCT/US2015/025003
§ 371 (c)(1),
(2) Date: Sep. 14, 2016

(87) PCT Pub. No.: WO2015/157467
PCT Pub. Date: Oct. 15, 2015

(65) Prior Publication Data
US 2017/0173312 A1 Jun. 22, 2017

Related U.S. Application Data

(60) Provisional application No. 61/977,990, filed on Apr. 10, 2014.

(51) Int. Cl.
*A61M 27/00* (2006.01)
*A61F 2/848* (2013.01)
(Continued)

(52) U.S. Cl.
CPC ............ *A61M 27/008* (2013.01); *A61F 2/848* (2013.01); *A61F 2/958* (2013.01); *A61M 25/04* (2013.01);
(Continued)

(58) Field of Classification Search
CPC ........ A61F 2/94; A61F 2002/048; A61F 2/04; A61F 2/82; A61M 27/008
See application file for complete search history.

(56) References Cited

U.S. PATENT DOCUMENTS 3,592,197 A * 7/1971 Cohen .................... A61F 2/0004
604/106
4,610,657 A * 9/1986 Densow .............. A61M 27/008
604/8
(Continued)

FOREIGN PATENT DOCUMENTS

WO 2003/075795 9/2003

OTHER PUBLICATIONS

U.S. Appl. No. 61/977,990, filed Apr. 10, 2014, Wan.
(Continued)

*Primary Examiner* — Alvin Stewart
(74) *Attorney, Agent, or Firm* — Dorsey & Whitney LLP

(57) ABSTRACT

Embodiments disclosed herein includes materials, devices, systems, and methods for utilizing a stent (100, 200, 300, 400, 500, 600, 700), reducing movement of a stent within an ureter, securing the stent within the ureter, aiding in insertion or retrieval of a stent from the ureter, preventing irritation of the trigone, or combinations thereof. In one embodiment, a stent is disclosed including at least one retaining structure (228, 328, 428, 528, 628, 728) positioned at least proximate a bladder configured to irritate a trigone less than a curled retaining structure.

30 Claims, 10 Drawing Sheets

(51) Int. Cl.
  *A61F 2/958* (2013.01)
  *A61M 25/04* (2006.01)
  *A61M 25/09* (2006.01)

(52) U.S. Cl.
  CPC ..... *A61M 25/09* (2013.01); *A61F 2002/8483* (2013.01); *A61F 2230/0067* (2013.01); *A61M 2025/09166* (2013.01)

(56) References Cited

U.S. PATENT DOCUMENTS

| | | | | |
|---|---|---|---|---|
| 4,790,809 | A * | 12/1988 | Kuntz | A61M 25/0045 600/434 |
| 4,820,262 | A * | 4/1989 | Finney | A61F 2/94 604/544 |
| 4,874,360 | A * | 10/1989 | Goldberg | A61M 27/008 604/544 |
| 5,052,998 | A * | 10/1991 | Zimmon | A61F 2/94 604/530 |
| 5,129,910 | A * | 7/1992 | Phan | A61B 17/22031 604/264 |
| 5,176,626 | A * | 1/1993 | Soehendra | A61F 2/94 604/286 |
| 5,322,501 | A * | 6/1994 | Mahmud-Durrani | A61M 25/04 604/544 |
| 5,531,741 | A * | 7/1996 | Barbacci | A61B 1/307 606/15 |
| 5,599,291 | A * | 2/1997 | Balbierz | A61L 27/34 604/264 |
| 5,681,274 | A * | 10/1997 | Perkins | A61M 25/00 604/264 |
| 5,769,882 | A * | 6/1998 | Fogarty | A61F 2/07 128/898 |
| 5,964,744 | A * | 10/1999 | Balbierz | A61L 27/34 604/530 |
| 5,984,965 | A * | 11/1999 | Knapp | A61B 17/22031 604/9 |
| 5,989,207 | A * | 11/1999 | Hughes | A61M 27/008 604/8 |
| 6,395,021 | B1 * | 5/2002 | Hart | A61F 2/04 604/8 |
| 9,259,517 | B2 * | 2/2016 | Li | A61L 31/145 |
| 9,585,742 | B2 * | 3/2017 | Nomura | A61F 2/94 |
| 9,789,293 | B2 * | 10/2017 | Teague | A61M 27/008 |
| 9,937,031 | B2 * | 4/2018 | Shelton | A61F 2/04 |
| 2001/0053936 | A1 * | 12/2001 | Whitmore, III | A61M 27/008 623/23.7 |
| 2003/0109930 | A1 * | 6/2003 | Bluni | A61F 2/04 623/23.7 |
| 2003/0120261 | A1 * | 6/2003 | Gellman | A61M 25/0017 604/544 |
| 2003/0171708 | A1 * | 9/2003 | Segura | A61M 27/002 604/8 |
| 2003/0176831 | A1 * | 9/2003 | Gellman | A61M 27/008 604/8 |
| 2003/0195456 | A1 * | 10/2003 | Robertson | A61F 2/04 604/8 |
| 2003/0199986 | A1 | 10/2003 | McWeeney et al. | |
| 2004/0059279 | A1 | 3/2004 | McWeeney et al. | |
| 2004/0143209 | A1 * | 7/2004 | Liu | A61M 27/008 604/8 |
| 2004/0181186 | A1 * | 9/2004 | Gellman | A61M 27/008 604/8 |
| 2004/0193092 | A1 * | 9/2004 | Deal | A61F 2/04 604/8 |
| 2005/0107736 | A1 * | 5/2005 | Landman | A61M 25/0068 604/93.01 |
| 2005/0124978 | A1 * | 6/2005 | Kim | A61M 25/0017 604/544 |
| 2008/0004578 | A1 | 1/2008 | Hixon et al. | |
| 2008/0051911 | A1 | 2/2008 | Rucker et al. | |
| 2013/0231752 | A1 | 9/2013 | Rosenbaum et al. | |
| 2014/0142721 | A1 * | 5/2014 | Robertson | A61L 31/145 623/23.66 |
| 2014/0277561 | A1 * | 9/2014 | Jordan | A61M 27/002 623/23.7 |
| 2015/0223953 | A1 * | 8/2015 | Pendleton | A61F 2/852 623/23.68 |
| 2015/0320357 | A1 * | 11/2015 | Kuraguntla | G01F 1/00 600/505 |
| 2016/0045347 | A1 * | 2/2016 | Smouse | A61F 2/95 623/23.66 |
| 2016/0128824 | A1 * | 5/2016 | Nomura | A61F 2/94 623/23.7 |
| 2016/0220397 | A1 * | 8/2016 | Nichols | A61M 27/008 |
| 2017/0095651 | A1 * | 4/2017 | Hutchins, III | A61M 31/002 |
| 2017/0105833 | A1 * | 4/2017 | Seguy | A61F 2/04 |
| 2017/0119554 | A1 * | 5/2017 | Davoudi | A61F 2/82 |
| 2017/0119559 | A1 * | 5/2017 | Seguy | A61F 2/94 |
| 2017/0173312 | A1 * | 6/2017 | Wan | A61M 25/09 |

OTHER PUBLICATIONS

International Search Report and Written Opinion from International Application No. PCT/US2015/025003 dated Jul. 24, 2015.

* cited by examiner

URETERAL STENTS

CROSS-REFERENCE TO RELATED APPLICATIONS

This application claims priority to U.S. Provisional Application 61/977,990 filed on 10 Apr. 2014, the disclosure of which is incorporated herein, in its entirety, by this reference.

BACKGROUND

Catheterization is a relatively common medical procedure for treating drainage from a tube or duct. In the case of ureteral catheterization, a ureteral stent and/or a catheter may prevent or treat an obstruction affecting urine, produced in the kidney, flowing to the bladder. In most cases, stents allow or restore the free flow of urine from the kidney. In some instances, catheterization may also facilitate injection of liquids into the kidney. Typically, ureteral catheterization is performed by inserting a stent through a patient's urethra into the bladder.

Stents can be used to prevent closure of a passage, tube, or duct. The diameter of a stent can be expanded after being positioned within the patient, or they can be self-expanding such as in response to a change in temperature. In most cases, stents are designed to maintain their diameter after deployment and positioning. Where the stent is expandable, the material of the stent may be deformed after deployment. Alternatively, the stent may be manufactured from an elastic or shape memory material. In other cases, the stent may be compressed within a sleeve that prevents expansion of the stent until it has been properly positioned within the patient. After deformation, the stent is designed to remain in the deployed state.

Stents are often used to prevent closure or obstruction of the ureter. In some cases, the ureter may be blocked, for example by a kidney stone. While opening the ureter to allow resolution of a kidney stone may require only temporary positioning of the stent (days or weeks), other conditions may require the stent to remain in the ureter for longer periods of time, for example several months or longer. In some cases, stents may be placed within the ureter to prevent spasms and/or collapse of the ureter after an operation, for example, an operation to remove a kidney stone.

Guidewires may be used to position a stent. In some cases, a guidewire may be inserted into the ureter. The stent may be positioned about the guidewire and advanced until it is properly positioned. In some cases, a cystoscope may aid in positioning the guidewire. In many cases, fluoroscopy may be used to help ensure proper placement of the guidewire prior to advancing the stent.

In some cases, a stent may move after being positioned in the ureter. For example, the stent may move towards the kidney or bladder. Movement of the stent may arise for various reasons. For example, movement of the stent may be caused by routine activity and/or from strenuous physical activity by the patient. Movement of the stent may cause the ureter to partially collapse in regions of the ureter vacated by the stent and/or the stent to irritate or damage the bladder (e.g. the trigone) or kidney.

In order to prevent or reduce movement of a stent or (maintain patency), one or both ends of the stent may be curled in a pigtail, spiral, or J-shape (i.e., a curled retaining structure). The curled retaining structure may prevent or reduce migration of the stent within the ureter. Stents having a curled retaining structure at the kidney end of the stent (e.g. first end) may prevent the stent from moving towards the bladder. A curled retaining structure positioned at the bladder end of the stent (e.g. second end) may prevent movement of the stent towards the kidney. Additionally structures at the bladder end of the (e.g., a coil, string) may also aid in retrieval and removal of the stent.

Stents may cause or contribute to patient discomfort and pain. For example, patient discomfort and pain may be attributed to the stent irritating the trigone area of the bladder. Irritation of the trigone may occur when the stent or a retaining structure (e.g. curl retaining structure), contacts the trigone. The trigone (or trigonum) is a triangular-shaped region located on the floor of the urinary bladder, and is roughly defined by the opening of the urethra and the two ureteral orifices. The trigone is believed to be particularly innervated and, therefore, is especially sensitive to irritation caused by pressure, such as contact with a stent.

In some cases, stents may result in urine reflux. Urine reflux may occur when urine travels from the bladder to the kidneys in response to retrograde pressure. Retrograde pressure occurs in the bladder when attempting to void the bladder of urine, and may transmit urine or other fluids up the stent to the kidney. In response to this pressure, the lower portion of the ureter, proximal the bladder, normally closes during routine voiding of the bladder, but the presence of a stent or catheter may interfere with this closure. This may lead to irritation of the ureter as well as urine reflux.

SUMMARY

Embodiments disclosed herein includes materials, devices, systems, and methods for utilizing a stent, reducing movement of a stent within an ureter, securing the stent within the ureter, aiding in insertion or retrieval of a stent from the ureter, preventing irritation of the trigone, or combinations thereof. In an embodiment, a ureteral stent is disclosed. The ureteral stent includes an elongated member. The elongated member defines a drainage lumen. The elongated member includes a first end. The first end includes a first retaining structure and a plurality of openings in fluid communication with the drainage lumen. The first end is configured to be positioned at least proximate a kidney. The elongated member further include a second end spaced longitudinally from the first end. The second end includes a second retaining structure and one or more openings in fluid communication with the drainage lumen. The second retaining structure is configured to irritate a trigone of a bladder less than a curled retaining structure.

In an embodiment, a method of inserting a stent into a ureter is disclosed. The method includes inserting a distal tip of a guidewire into a bladder and up a ureter. The guidewire including a plurality of marker structures having a known length between the each of the marker structures. The plurality of marker structures are configured to be visualized by a practitioner using a visualization technique. The method further includes positioning the distal tip of the guidewire into a kidney that is drained by the ureter. The method also includes visualizing the plurality marker structures using the visualizing technique. Additionally, the method includes measuring the length of the ureter using the plurality of marker structures. The method further includes selecting a stent including a first end and a second end spaced longitudinally from the first end. The stent having a length selected to have a first portion of the stent positioned in the kidney and a second portion positioned in the ureter, with the first portion including the first end. The method also includes positioning the stent on the guidewire. Finally, the method includes advancing the stent on the guidewire until the first portion of the stent is positioned in the kidney and the second portion of the stent within the ureter.

In an embodiment, a method of retrieving a stent positioned in a ureter is disclosed. The method includes providing a stent at least partially positioned in the ureter. The stent include a first end and a second end spaced longitudinally from the first end. The first end is positioned at least proximate to the kidney. The second end of the stent includes a first magnetically attractable structure. The method further includes inserting a distal end of a retrieving device into a bladder. The retrieving device includes a second magnetically attractable structure at or near the distal end thereof. The method also includes positioning the distal end of the retrieving device at least proximate to the second end of the stent such that the first and second magnetically attractable structures are magnetically attracted to each other. Additionally, the method includes applying a pulling force to the retrieving device to retrieve the stent from the ureter.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Embodiments disclosed herein includes materials, devices, systems, and methods for utilizing a stent, reducing movement of a stent within an ureter, securing the stent within the ureter, aiding in insertion or retrieval of a stent from the ureter, preventing irritation of the trigone, or combinations thereof.

Figure 1A:
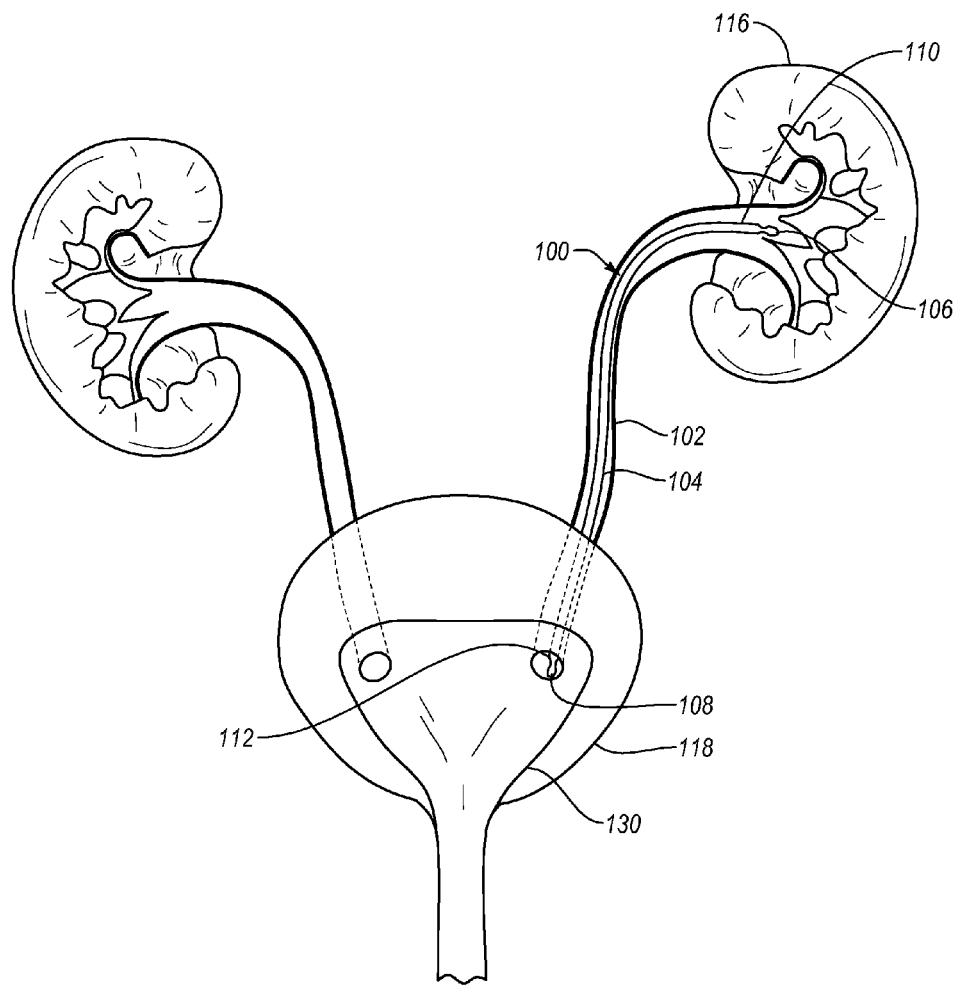
FIGS. 1A and 1B are schematic illustrations of a stent at least partially positioned within a ureter and the stent, respectively, according to an embodiment.
Figure 1B:
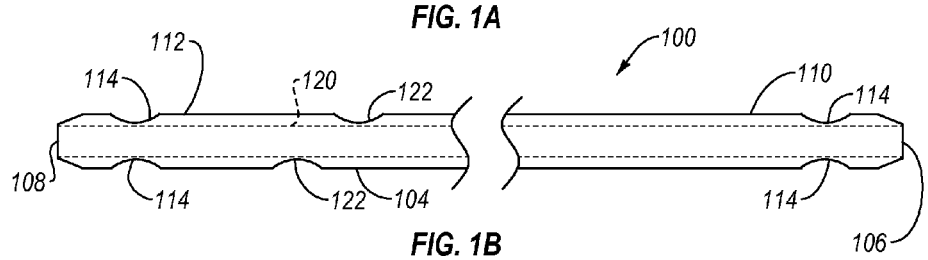

FIGS. 1A and 1B are schematic illustrations of a stent 100 at least partially positioned within a ureter 102 and the stent 100, respectively, according to an embodiment. The stent 100 includes an elongated member 104 including a first tip 106 and a second tip 108 spaced longitudinally from the first tip 106. The elongated member 104 furthers includes a first end 110 that includes the portion of the elongated member 104 at and proximate to the first tip 106. Similarly, the elongated member 104 includes a second end 112 that includes a portion of the elongated member 104 that is at and proximate to the second tip 108. The elongated member 104 defines a drainage lumen 120 that extends at and from the first tip 106 to at and including the second tip 108. The first end 110 may include one or more openings or ports 114 therein that allow a fluid (e.g., urine from a kidney 116) to enter the elongated member 104 via the drainage lumen 105. The second end 112 may also include one or more openings or ports 114 that allow the fluid to exit the elongated member 104 via the drainage lumen 105. In an embodiment, at least some of the one or more openings 114 may be located at the first tip 106 and/or the second tip 108.

Portions of the elongated member 104 may be configured to be at least partially positioned within the ureter 102, the kidney 116, the bladder 118, or combinations thereof. For example, the first end 110 may be configured to be positioned at, near, or within a patient's kidney 116. Similarly, the second end 112 may be configured to be positioned at, near, or within a patient's bladder 118.

The drainage lumen 120 is configured to drain a fluid from the patient's kidney 116 into the patient's bladder 118. As such, the lumen 120 may extend between at least the first end 110 and the second end 112. For example, the lumen 120 may extend between the one or more openings 114 of the first end 110 and the one or more openings 114 of the second end 112 and be in fluid communication with the one or more openings 114. The drainage lumen 120 may include various structures therein that facilitate movement of the fluid through the stent 100. In an embodiment, the drainage lumen 120 may include one or more valves (not shown) positioned therein that prevent or allow the flow of the fluid. In an embodiment, the drainage lumen 120 may include one or more ports 122 positioned along the drainage lumen 120. The one or more ports 122 may permit fluid between the stent 100 and the ureter 102 to access the drainage lumen 120. For example, the one or more ports 122 may allow urine reflux to enter the drainage lumen 120.

The elongated member 104 may include one or more walls having a constant or varying thickness that define the drainage lumen 120. For example, portions of the one or more walls (e.g. near the first end 110) may be sufficiently thick to resist kinking despite constriction or other manipulation of the stent 100 due to enlargement of tissue surrounding it, or due to peristaltic motions. The one or more walls may also be sufficiently thick to resist kinking during insertion and removal of the stent 100. In an embodiment, the one or more walls may include an annular wall that may resist collapsing upon itself and sealing the drainage lumen 120 upon application of a radial, lateral or longitudinal pressure. The radial, lateral, or longitudinal pressure may be applied by the surrounding tissue during insertion, positioning, and/or removal of the stent 100.

Figures 2A, 2B:
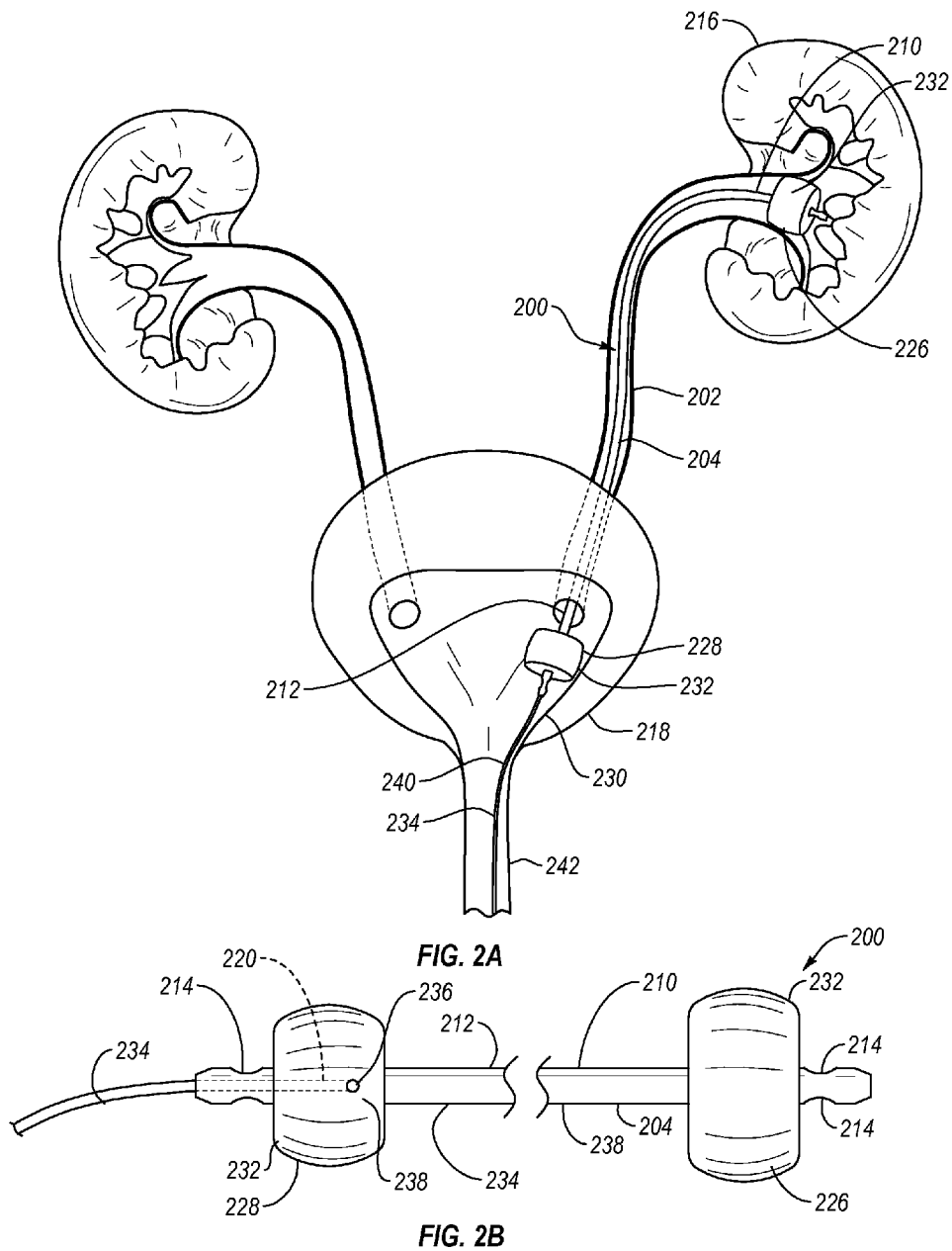
FIGS. 2A and 2B are schematic illustrations of a stent including a balloon structure positioned within a ureter and the stent, respectively, according to an embodiment.

The stent 100 may include one or more retaining structures (e.g., the first retaining structure 226 and the second retaining structure 228 shown in FIG. 2B or any other retaining structure disclosed herein) that may prevent the stent from migrating towards the kidney 116 or the bladder 118. For example, the first end 110 may include one or more retaining structures (e.g., the first retaining structure 226 shown in FIG. 2B or any other retaining structure disclosed herein) configured to position the first end 110 within the kidney 116. As such, the one or more retaining structures may prevent or reduce migration of the stent 100 towards the bladder 118. In an embodiment, the second end 112 may also include one or more retaining structures (e.g., the second retaining structure 228 shown in FIG. 2B or any other retaining structure disclosed herein). As such, the one or more retaining structures may also be configured to reduce irritation of trigone 130 compare to a curled retaining structure (e.g. a pigtail, spiral, or J-shape). Additionally, such one or more retaining structures may prevent or reduce migration of the stent 100 towards the kidney 116. In an embodiment, the one or more retaining structures may be integral with or distinct from the rest of the first end 110 or the second end 112. In an embodiment, the one or more retaining structures may be configured to allow urine to flow around the one or more retaining structures and between the stent 100 and a wall of the ureter 102. In an embodiment, as disclosed herein, the one or more retaining structures may include one or more balloons, sponges, flaps, barbs, tabs, or weighted ends that may help in preventing or reducing movement of the stent 100 within the ureter 102. In an embodiment, the one or more retaining structures include a suture structure for attaching the stent 100 to the ureter 102.

The stent 100 may be formed from one or more materials. In an embodiment, the stent 100 is manufactured from one or more biocompatible plastics or polymers. For example, the stent 100 may be formed from ethylene vinyl acetate (EVA), polytetrafluoroethylene (PTFE), silicone polyurethane, polyamide, polyurethane plastics, polyethylene plastics, and other thermoplastics and block copolymers thereof. In an embodiment, the stent 100 is made from a metallic material such as stainless steel. In an embodiment, the stent 100 may be manufactured from a superelastic or shape memory material. For example, a nickel-titanium alloy (e.g., nitinol) is a suitable superelastic or shape memory alloy for manufacturing the stent 100 therefrom. In an embodiment, at least one portion of the stent 100 may be coated.

In an embodiment, the one or more retaining structures may be formed from one or more materials. For example, the one or more retaining structures may be formed from a second biocompatible material. The second biocompatible material may include a hydrophilic polymer, such as polyurethane, nylon, polycarbonate, poly(ethylene oxide), polyvinyl pyrrolidone, polyvinyl alcohol, poly(ethylene glycol), polyacrylamide, poly(hydroxyethylacrylate), copolymers thereof, or combinations thereof. The second biocompatible material may also include silicone or a similar polymer. The one or more retaining structures may include a material configured to reduce irritations of the trigone 130. In an embodiment, at least a portion of the one or more retaining structures may be coated.

The stent 100 and/or the one or more retaining structures may be formed from a material that is readily deformable. In an embodiment, the stent 100 and/or the one or more retaining structures may be formed from a material exhibiting a Shore hardness between about 60 A and about 85 A, or alternately between 20 Shore D and 65 Shore D.

Patency—Retention Structures

Balloon Structure Embodiments

FIGS. 2A and 2B are schematic illustrations of a stent 200 positioned within a ureter 202 and the stent 200 including a balloon structure 232, respectively, according to an embodiment. The stent 200 may be substantially similar to or the same the stent 100 shown in FIG. 1B. For example, the stent 200 may include an elongated member 204 having a first end 210 and a second end 212. The elongated member 204 may define a lumen 220 extending therethrough. Additionally, the first end 210 and the second end 212 may include one or more openings 214 formed therein.

In an embodiment, the first end 210 may include a first retaining structure 226 and the second end 212 may include a second retaining structure 228. In the illustrated embodiment, each of the first retaining structure 226 and the second retaining structure 228 includes a balloon structure 232. However, the first retaining structure 226 can include any of the retaining structures disclosed herein. The balloon structure 232 may include one or more inflatable balloons. The first retaining structure 226 may include the balloon structure 232 configured to be positioned and at least partially inflated in the patient's kidney 216. As such, the first retaining structure 226 may prevent or reduce movement of the stent 200 towards the bladder 218. The second retaining structure 228 may also include the balloon structure 232 configured to be positioned and at least partially inflated in the patient's bladder 218. As such, the second retaining structure 228 may be configured to reduce or prevent irritation of trigone 230. Additionally, the second retaining structure 228 may also be configured to prevent or reduce movement of the stent 200 towards the kidney 216.

The balloon structure 232 may surround at least a portion of the stent 200 and may be attached to the first end 210 and/or the second end 212 of the stent 200. In an embodiment, the balloon structure 232 may be positioned circumferentially about the stent 200, such that the stent 200 passes through the balloon structure 232. In an embodiment, the balloon structure 232 may surround only a portion of the stent 200 such that the balloon structure 232 does not completely envelope the stent 200.

The balloon structure 232 may be configured to be inflated with an inflation fluid, such as air, saline, another biocompatible fluid, or another appropriate inflation fluid after the stent 200 is at least partially positioned within the ureter 202. In an embodiment, the stent 200 may include an inflation tube 234 that is in fluid communication with each of the balloon structures 232 and enables an inflation fluid to inflate the at least one balloon structure 232. The inflation tube 234 may include a channel or a lumen that allows the inflation fluid to flow therein. The inflation tube 234 may also include one or more holes 236 therein that allow the inflation fluid to flow from the inflation tube 234 into the balloon structure 232.

In an embodiment, the inflation tube 234 may include a distal portion 238 that is coupled to and proximate to at least one balloon structure 232, a proximal portion (not shown) that is spaced from the distal portion 238, and an intermediate portion 240 that extends between the distal portion 238 and the proximal portion. The distal portion 238 may include the one or more holes 236 therein. The distal portion 238 may be configured to be attached to, enclosed by, or incorporated into the elongated member 204. For example, the elongated member 204 may define two lumens: the first lumen (e.g. lumen 220) may be configured to conduct urine from the kidney 216 to the bladder 218 and the second lumen may incorporate or enclose the inflation tube 234. In the illustrated embodiment, the distal portion 238 of the inflation tube 234 may be incorporated into or enclosed by the second lumen. In an embodiment, the cross-sectional area of the first lumen may form a major portion of the cross-sectional area of the elongated member 204.

In the illustrated embodiment, the intermediate portion 240 extends from the second retaining structure 228 towards the urethra 242 and out the patient. In such an embodiment, the proximal portion of the inflation tube 234 may be positioned outside the patient or another location that allows a practitioner (e.g., a doctor) to access the proximal portion. The practitioner may use the proximal portion to insert an inflation fluid into and/or flow an inflation fluid through the inflation tube 234. For example, the proximal portion may include a pump or enable the practitioner to insert an inflation fluid via a syringe.

In an embodiment, the balloon structure 232 and/or the inflation tube 234 may include a device configured to enable or prevent the flow of the inflation fluid used to inflate the balloon structure 232. For example, at least one of the balloon structures 232 or the inflation tube 234 may include a valve (not shown). The valve may be configured to open or close in response to direction from a practitioner. For example, the valve may be located on the proximal portion of the inflation tube 234. In an embodiment, the valve may release the inflation fluid from the balloon structure 232 when a pressure applied to the balloon structure 232 is above a threshold. In an embodiment, the valve may release the inflation fluid from the balloon structure 232 into a body cavity of the patient, the lumen 220 or the inflation tube 234.

Prior to inflation, the disclosed balloon structure 232 exhibits a small profile and is sufficiently flexible to allow it to safely travel into and through the urethra 242 and the ureter 202. For example, prior to inflation, the balloon structure 232 may exhibit an outer diameter that is substantially similar to or slightly larger than the diameter of the elongated member 204. Upon at least partially positioning the stent 200 within the ureter 202, one or both of the balloon structures 232 shown in FIG. 2A may be inflated, thereby anchoring the stent 200 in position. The balloon structure 232 may be deflated to remove the stent 200 from the ureter 202. For example, the balloon structure 232 may be deflated by actively removing the inflation fluid (e.g. using a valve, the pump, or syringe). Alternatively, the balloon structure 232 may be deflated by puncturing the balloon.

In some embodiments, the balloon structure 232 may include a relief structure (not shown). The relief structure may include at least one groove extending at least transversely in the longitudinal direction of the balloon in order to provide flexibility in a direction transverse to the longitudinal direction. In some embodiments, the relief structure may be produced by applying heat or high pressure to the inside of the balloon structure 232, which may deform the balloon structure 232. The relief structure may also be produced by winding a wire around at least a portion of the balloon structure 232, for example in the form of a helix, or by at least partially enclosing the balloon structure 232 in a counter-pressure body.

Sponge Structure Embodiments

Figure 3A:
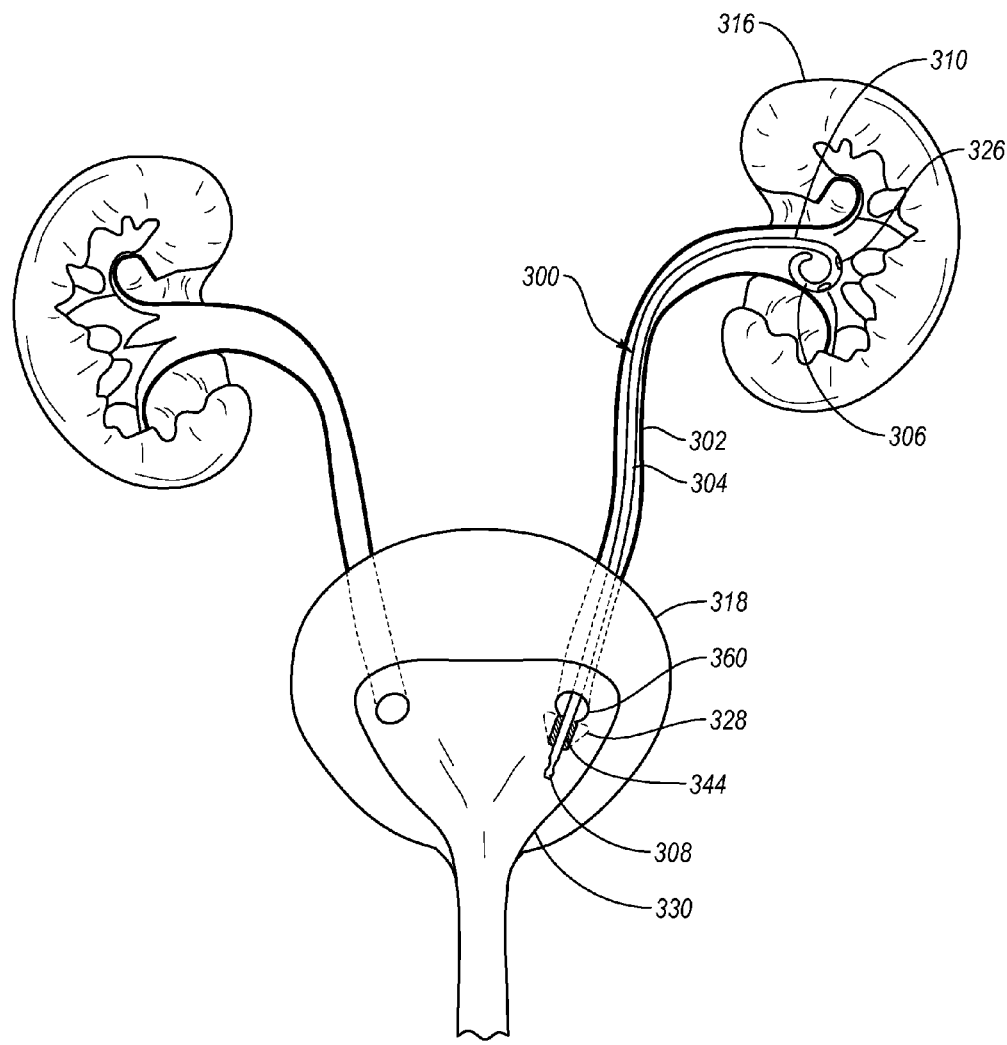
FIGS. 3A and 3B are schematic illustrations of a stent including a sponge structure positioned in a ureter and the stent, respectively, according to an embodiment.
Figure 3B:
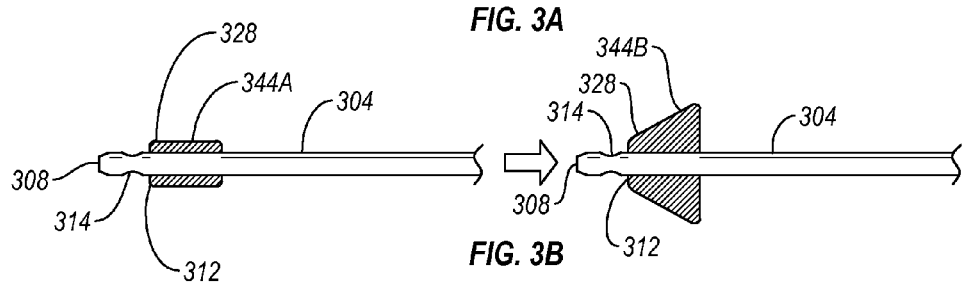

FIGS. 3A and 3B are schematic illustrations of a stent 300 positioned in a ureter 302 and the stent 300 including a sponge structure 344, respectively, according to an embodiment. The stent 300 may be substantially similar to or the same as the stent 100 shown in FIG. 1B. For example, the stent 300 may include an elongated member 304 having a first end 310 and a second end 312. Additionally the first end 310 and the second end 312 may include one or more openings 314 formed therein.

In an embodiment, the first end 410 includes a first retaining structure 326 and the second end 312 includes a second retaining structure 328. In the illustrated embodiment, the first retaining structure 326 includes a curled retaining structure positioned in the patient's kidney 316. However, the first retaining structure 326 may include any retaining structure disclosed herein. The second retaining structure 328 includes a sponge structure 344 positioned in the patient's bladder 318 of the patient. The sponge structure 344 includes at least a sponge or another material that absorbs moisture. The sponge structure 344 may be configured to irritate a trigone 330 when the sponge structure 344 contacts the trigone 330 than a curled retaining structure. For example, the sponge structure 344 may include a material that is less likely to irritate the trigone 330.

In an embodiment, the sponge structure 344 is initially compacted to facilitate insertion of the stent 300 through at least the urethra 342. For example, as illustrated in FIG. 3B, the compacted sponge structure 344A may exhibit an outer diameter that is slightly larger (e.g. less than 3× larger or less than 2× larger) than a diameter of the elongated member 304. After being inserted into a patient, the compacted sponge structure 344A may absorb moisture from bladder 318 or another source (e.g., urine flowing through the stent 300). The compacted sponge structure 344A may expand into an expanded sponge structure 344B as the sponge structure 344 absorbs the moisture. Expansion of the sponge structure 344 may prevent or reduce movement of the stent 300 towards the kidney 316.

The sponge structure 344 may exhibit a plurality of shapes. In an embodiment, the compacted sponge structure 344A may exhibit a shape that may enable easy insertion of the stent 300 into the patient. For example, the compacted sponge structure 344A may exhibit a small profile and include a sufficiently flexible material that allows the compacted sponge structure 344A to safely travel into and through at least the urethra 342. In an embodiment, the expanded sponge structure 344B may exhibit a shape that may prevent or reduce movement of the stent 300 towards the kidney 316. In such an embodiment, the expanded sponge structure 344B may exhibit an outer diameter that is larger than the diameter of the elongated member 304 and/or ureteral orifice 360. In an embodiment, the expanded sponge structure 344B may include an outer diameter that varies with distance from the second tip 308. For example, the expanded sponge structure 344B may exhibit an outer diameter that decreases with increased proximity to the second tip 308. This general conical shape, as well as other suitable shapes, may facilitate removal of the stent 300.

The sponge structure 344 may allow a fluid (e.g., urine) to flow through the stent 300 (e.g., through the lumen 320)

and/or around the stent 300. In an embodiment, the sponge structure 344 may allow the fluid to flow through the sponge structure 344 and into the lumen 320. For example, the sponge structure 344 may be positioned over one or more openings 314. In another embodiment, the sponge structure 344 may be positioned circumferentially around the stent 300, such that the stent 300 may pass through the sponge structure 344. In an embodiment, the sponge structure 344 may be discontinuously positioned about the stent 300. For example, the sponge structure 344 may include a one or more sponges (e.g., one, two, or more sponges). In an embodiment, the sponge structure 344 may be attached to a first tip 306 of the stent 300 and/or a second tip 308 of the stent 300 and extend away from the elongated member 104.

Flared Structure Embodiments

Figure 4A:
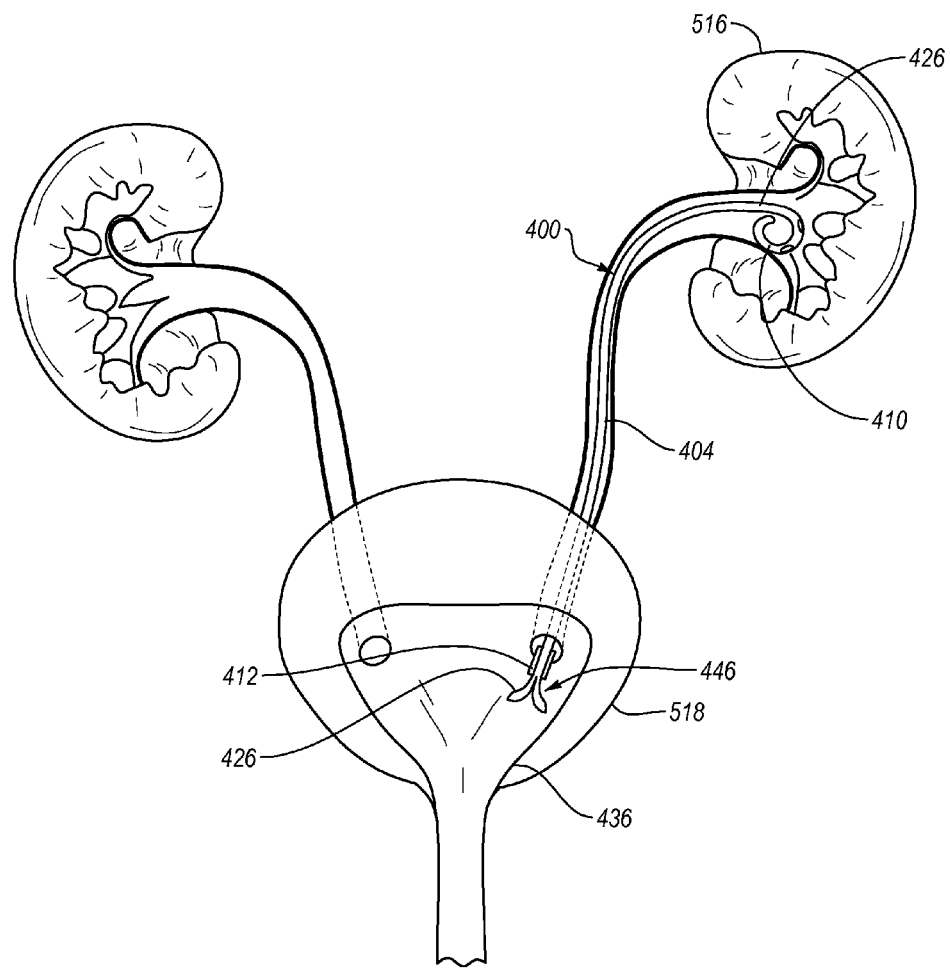
FIGS. 4A and 4B are schematic illustrations of a stent at least partially positioned in a ureter and the stent including a flared structure, respectively, according to an embodiment.
Figure 4B:
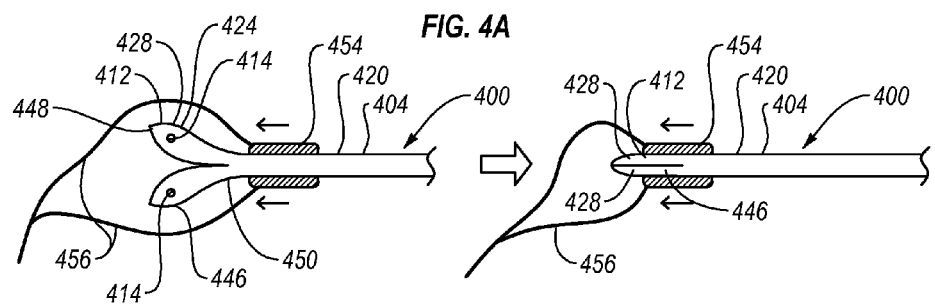

FIGS. 4A and 4B are schematic illustrations of a stent 400 at least partially positioned in a ureter 402 and the stent 400 including a flared structure 446, respectively, according to an embodiment. The stent 400 may include an elongated member 404 having a first end 410 and a second end 412. The elongated member 404 may define a lumen 420. Additionally the first end 410 and the second end 412 may include one or more openings 414 formed therein.

In an embodiment, the first end 410 includes a first retaining structure 426 and the second end 412 includes a second retaining structure 428. In the illustrated embodiment, the first retaining structure 426 includes a curled retaining structure positioned in a patient's kidney 416. However, the first retaining structure 426 may include any retaining structure included herein. The second retaining structure 428 may include a flared structure 446 positioned in a patient's bladder 418. The flared structure 446 may include one or more flaps, barbs, tabs, or similar structures. The flared structure 446 may be configured to reduce irritation of a trigone 430 compared to when pigtail ends contact the trigone 430. The first retaining structure 426 and the second retaining structure 428 may prevent or reduce movement of the stent 400.

The flared structure 446 may include a maximum outer diameter that, when uncompressed, is greater than the diameter of the elongated member 404. As such, the flared structure 446 may prevent or reduce movement of the stent 400. For example, the flared structure 446 may include two or more flaps. Such a flared structure 446 may include a proximal end 448 and a distal end 450 that is spaced from the proximal end 448. The distal end 450 may be coupled to the rest of the elongated member 404 and may exhibit an outer diameter that is substantially similar to the diameter of the elongated member 404. The proximal end 448 may exhibit the maximum outer diameter that is substantially greater than the diameter of the elongated member 404. The maximum outer diameter of the flared structure 446, when uncompressed, may be large enough to prevent the stent 400 from moving towards the bladder 418.

In an embodiment, the flared structure 446 may include one or more openings 414 formed therein that are fluidly coupled to the lumen 420 of the stent 400. As such, the one or more openings 414 may be configured to drain urine from the kidney 416 into the bladder 418. In an embodiment, the flared structure 446 may expose a portion of the lumen 420. For example, an opening may be formed where the flared structure 446 exposes the lumen 420.

In an embodiment, the flared structure 446 may be configured to be compressible. For example, the flared structure 446 may include two or more flaps that may be compressed together. In such an embodiment, the stent 400 may include a collar structure 454 disposed about the exterior of the stent 400. The collar structure 454 may be configured to move along the exterior of the stent 400. For example, the collar structure 454 may include a string 456 attached thereto that moves the collar structure 454 towards the second end 412 when the string 456 is pulled. Pulling the string 456 may cause the collar structure 454 to contact the flared structure 446. Upon contacting the flared structure 446, further movement of the collar structure 454 towards the flared structure 446 may cause portions of the flared structure 446 to be compressed together. In one embodiment, when the collar structure 454 is completely positioned over the flared structure 446, the maximum outer diameter of the flared structure 446 may be substantially similar to the diameter of the elongated member 404.

Short Stent Embodiments

Figure 5A:
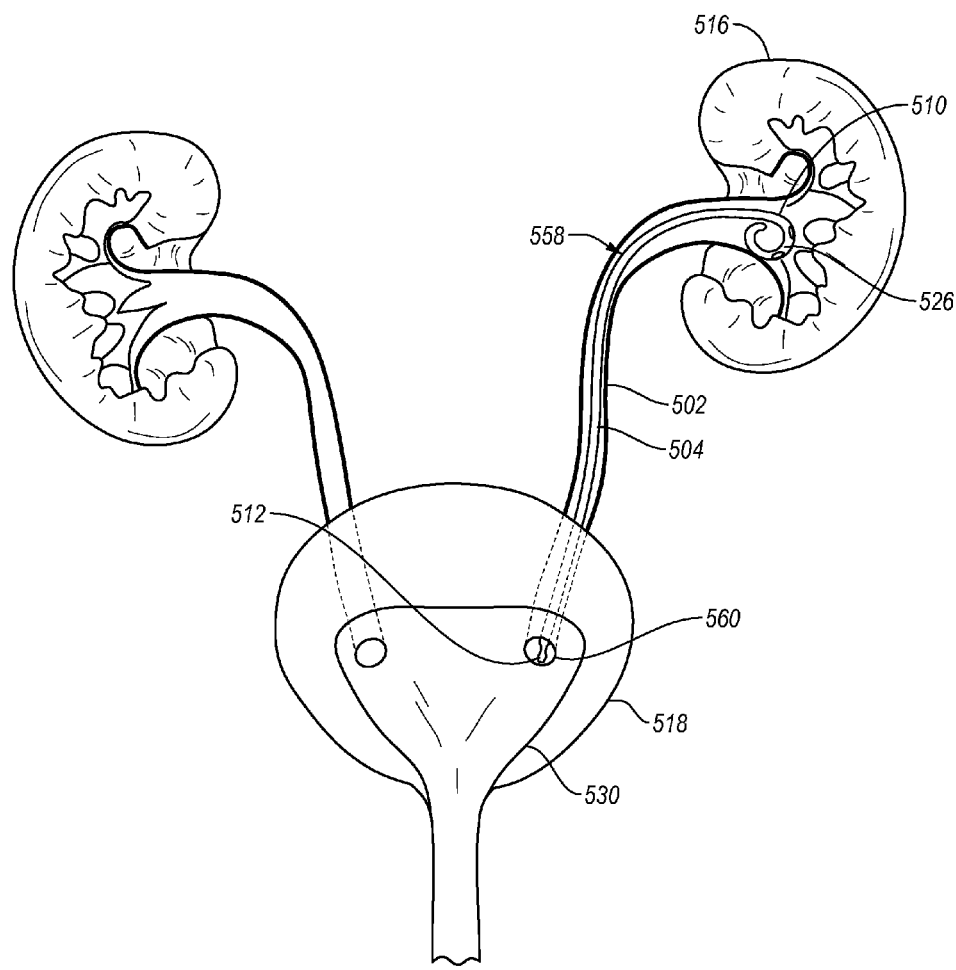
FIGS. 5A and 5B are schematic illustrations of a shortened stent at least partially positioned within a ureter, according to an embodiment.
Figure 5B:
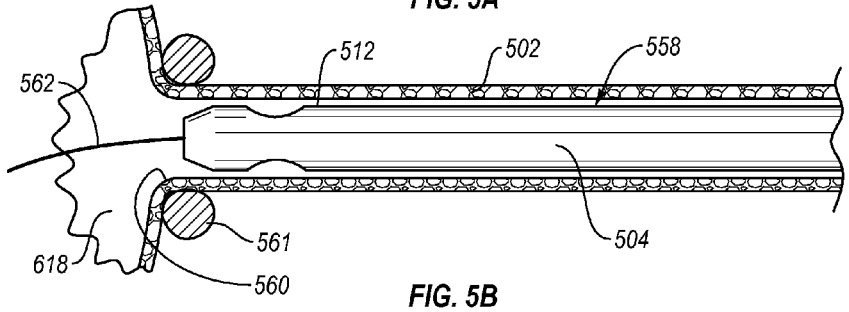

FIGS. 5A and 5B are schematic illustrations of a shortened stent 558 at least partially positioned within a ureter 502, according to an embodiment. The shortened stent 558 may include an elongated member 504. The elongated member 504 may include a first end 510 and a second end 512 spaced from the first end 510. The first end 510 may include a first retaining structure 526 that includes a curled retaining structure. However, the first retaining structure 526 may include any retaining structure disclosed herein.

In an embodiment, the shortened stent 558 may exhibit a length that prevents the first end 510 from being positioned in the patient's kidney 516 while the second end 512 is simultaneously positioned in the patient's bladder 518. For example, when the first end 510 is positioned in the patient's kidney 516, the second end 512 may be positioned within the ureter 502.

The shortened stent 558 may reduce patient pain and discomfort. In an embodiment, the shortened stent 558 reduces patient pain and discomfort because the second end 512 does not extend into the bladder 518. As such, the second end 512 does not irritate the trigone 530. In an embodiment, the shortened stent 558 may reduce patient pain and discomfort because the shortened stent 558 may reduce or prevent urine reflux. For example, the shortened stent 558 may exhibit a length that prevents the second end 512 from significantly affecting or disrupting the operation of ureteral orifice valve 561 (e.g. enables a ureteral orifice valve 561 to exhibit at least 50% normal function and/or reduce reflux). For example, the shortened stent 558 may exhibit a length that enables to ureteral orifice valve 561 to at least partially close the ureteral orifice 560, such as substantially completely closing the ureteral orifice 560.

In an embodiment, the second end 512 may include a device that facilitates retrieval of the shortened stent 558. For example, the second end 512 may include a retrieval string 562 attached thereto. The pulling the retrieval string 562 may retrieve the shortened stent 558. In an embodiment, the second end 512 may also include additional removal devices disclosed herein (e.g., the first magnetically attractable structure 766 shown in FIG. 7B).

In an embodiment, the shortened stent 558 may include a second retaining structure (not shown) that prevents or reduces migration of the shortened stent 500 towards the kidney 516. The second retaining structure may include any of the retaining structures disclosed herein. For example, the second retaining structure may include a flared structure similar to the flared structure 446 shown in FIG. 4B. The flare structure may contact and/or interact with a wall of the ureter to prevent or reduce migration of the shortened stent 558 towards the kidney 516. In another embodiment, the second retaining structure may include a weighted second end that prevents or reduces migration of the shortened stent 558 towards the kidney 516. The weighted second end may exhibit a mass that is greater than another portion of the elongated member 504 having a similar length.

Dissolvable Sutures Embodiments

Figure 6A:
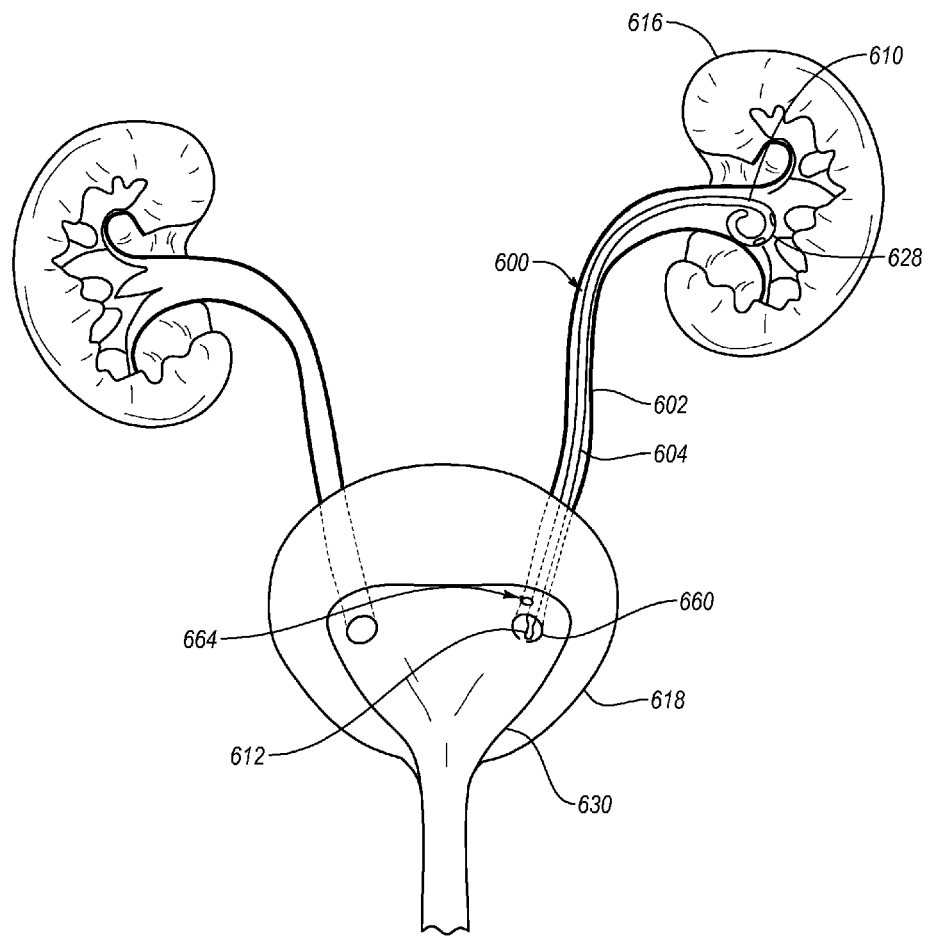
FIGS. 6A and 6B are schematic illustrations of a stent at least partially positioned in the ureter and the stent including a suture structure, respectively, according to an embodiment.
Figure 6B:
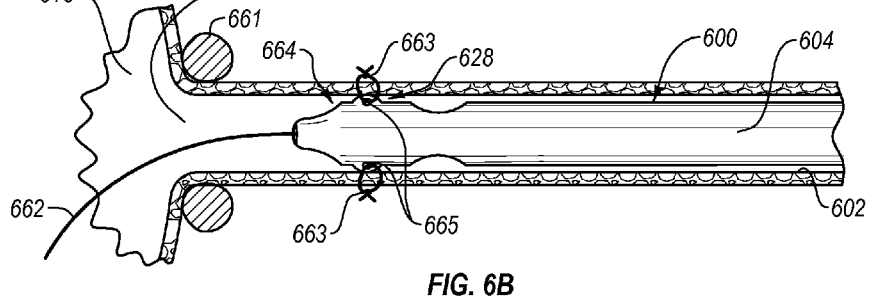

FIGS. 6A and 6B are schematic illustrations of a stent 600 at least partially positioned in the ureter 602 and the stent 600 including a suture structure 664, respectively, according to an embodiment. The stent 600 may include an elongated member 604 having a first end 610 and a second end 612. The first end 610 can include a first retaining structure 626 configured to prevent or reduce movement of the stent 600 towards a bladder 618. The first retaining structure 626 may include any of the retaining structures disclosed herein.

In an embodiment, the second end 612 includes a second retaining structure 628. The second retaining structure 628 may include a suture structure 664. The suture structure 664 may be configured to prevent or reduce migration of the stent 600 towards kidney 616. In an embodiment, the second retaining structure 628 including the suture structure 664 may also prevent or reduce migration of the stent 600 towards the bladder 618. The suture structure 664 may enable a practitioner (e.g. a doctor) to secure the stent 600 within the body using one or more sutures. As such, the suture structure 664 may at least include at least one suture 663 and a structure 665 on the stent 600 (e.g., a hole) that couples the at least one suture to the stent 600. The suture structure 664 may attach the stent 600 to the bladder 618, at or near an opening to ureteral orifice 660, or within the ureter 602. In an embodiment, the suture structure 664 includes at least one dissolvable suture. In an embodiment, the suture structure 664 may additionally include one or more attachment structures that further secure the stent in place. For example, the one or more attachment structures include a tab, a balloon, a flap, a barb, etc.

In an embodiment, the suture structure 664 may be used with a stent that is substantially similar to or the same as the shortened stent 558 shown in FIG. 5B. For example, the second end 612 of the stent 600 may be positioned in the ureter 602 and the suture structure 664 may be attached to a wall of the ureter 602. As such, the stent 600 may not significantly affect or disrupt normal operation of ureteral orifice valve 661, thereby reducing or eliminating urine reflux. In an embodiment, the suture structure 664 may be used with a stent that is substantially similar to the stent 100 shown in FIG. 1A. For example, the second end 612 of the stent 600 may be at least partially positioned in the bladder 618 and the suture structure 664 may attach the stent 600 to the bladder 618, the ureteral orifice 660, or the ureter 602.

In some embodiments, use of the suture structure 664 may reduce patient pain and discomfort because contact between the stent 600 and a trigone 630 is reduced or eliminated. As such, the suture structure 664 may reduce irritation of the trigone 630 compared to a curled retaining structure.

The stent 600 may be removed by various methods. In an embodiment, the stent 600 may be removed after one or more suture has dissolved or starts dissolving. For example, the stent 600 may include a removal string 662 attached thereto. Pulling on the removal string 662 may retrieve the stent 600 after one or more sutures have dissolved or start dissolving. Different sutures having differing dissolve times may be used depending upon the length of time the stent 600 is intended to reside within the ureter 602.

Retrieval

Magnetic Stent Embodiments

Figure 7A:
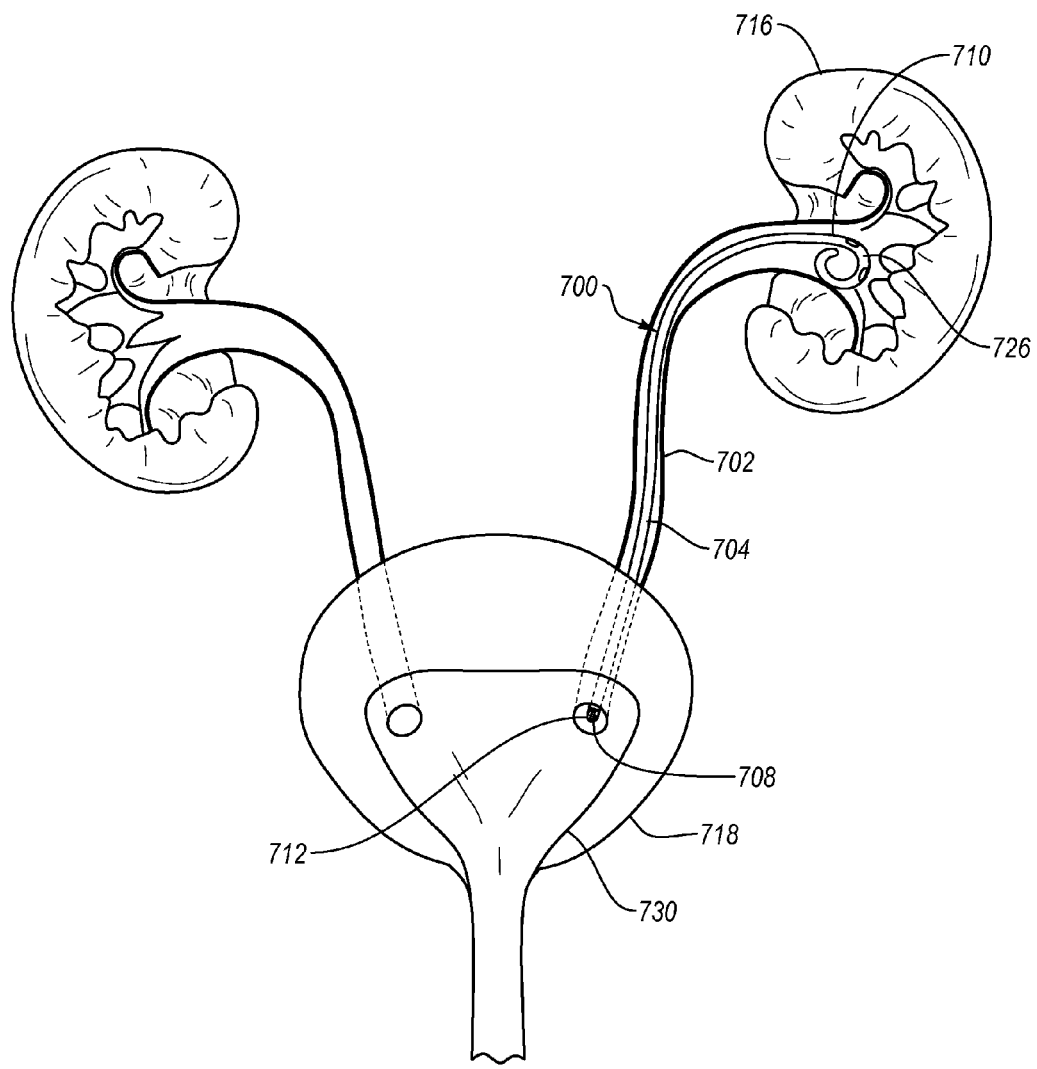
FIGS. 7A and 7B are schematic illustrations of a stent that is at least partially positioned in a ureter and the stent including a first magnetically attractable structure, respectively, according to an embodiment.
Figure 7B:
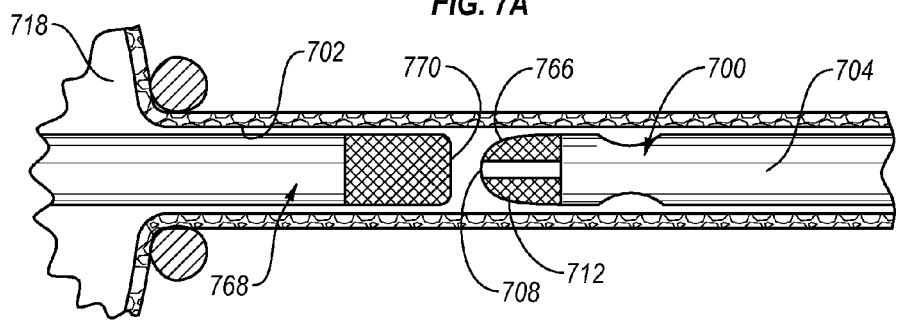

FIGS. 7A and 7B are schematic illustrations of a stent 700 that is at least partially positioned in a ureter 702 and the stent 700 including a first magnetically attractable structure 766, respectively, according to an embodiment. The stent 700 may include an elongated member 704 having a first end 710 and a second end 712. The first end 710 can include a first retaining structure 726 configured to be positioned, for example, in a kidney 716 of a patient. The first retaining structure 726 may prevent or reduce movement of the stent 700 towards the bladder 718. The first retaining structure 726 may include any retaining structure discussed herein. The second end 712 may include a second retaining structure (not shown). For example, the stent 700 may include a weighted second end 712. In the illustrated embodiment, the stent 700 may be substantially similar to or the same as the shortened stent 558 shown in FIG. 5B. However, in some embodiments, the stent 700 may be substantially similar to or the same as the stent 100 shown in FIG. 1B.

In an embodiment, the second end 712 may include a first magnetically attractable structure 766 positioned at or near the second tip 708. The first magnetically attractable structure 766 may be configured to be retrieved from within the ureter 702 using magnetic attraction. For example, the first magnetically attractable structure 766 may include at least one magnet, at least one magnetically attractable material (e.g., a metal, an iron-based material, or other suitable ferromagnetic material), or combinations thereof.

The stent 700 may be removed from the ureter 702 using a retrieving device 768. In an embodiment, the retrieving device 768 may include a catheter. A portion of the retrieving device 768 configured to contact the stent 700 may include a second magnetically attractable structure 770. In an embodiment, the second magnetically attractable structure 770 may include at least one magnet, at least one magnetically attractable material, or combinations thereof. When the second magnetically attractable structure 770 is positioned at least proximate the first magnetically attractable structure 766, the magnetic attraction between the first magnetically attractable structure 766 and the second magnetically attractable structure 770 may pull the stent 700 towards the retrieving device 768. For example, when the second magnetically attractable structure 770 contacts the first magnetically attractable structure 766, the magnetic attraction between the first magnetically attractable structure 766 and the second magnetically attractable structure 770 may be sufficiently strong to allow the stent 700 to be removed from the ureter 702 by applying a pulling force to the retrieving device 768 away from the kidney 716.

In an embodiment, the first magnetically attractable structure 766 and the second magnetically attractable structure 770 may both include a magnet. In such an embodiment, the polarity of both magnets may be oriented such that, when both magnets are in close proximity or are in contact, the magnetic attraction therebetween is sufficiently strong to remove the stent 700.

Figure 7C:
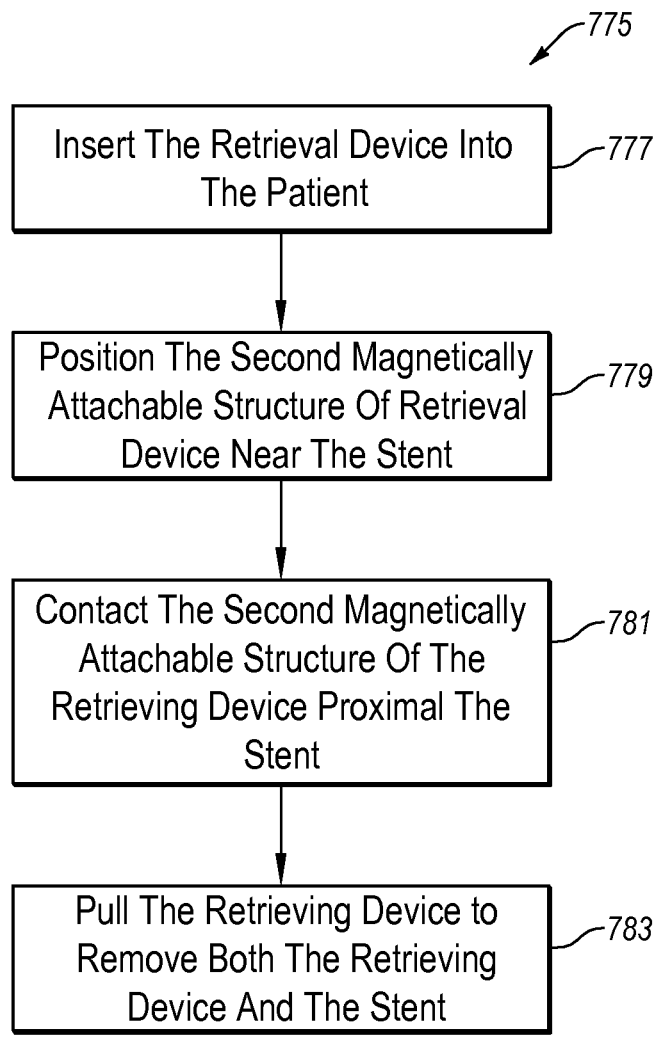
FIG. 7C is a flow diagram of a method of retrieving a stent from a ureter using a magnetically attractable structure, according to an embodiment.

FIG. 7C is a flow diagram of a method 775 of retrieving the stent 700 from the ureter 702 using the first magnetically attractable structure 766, according to an embodiment. The patient may already have the stent 700, including the first magnetically attractable structure 766, at least partially positioned in the patient's ureter 702. In act 777, the method 775 includes inserting the retrieving device 768 into the patient. In act 779, a practitioner (e.g., a doctor) may position the second magnetically attractable structure 770 of the retrieving device 768 proximate to the stent 700. In act 781, the practitioner may contact the second magnetically attractable structure 770 of the retrieving device 768 to the first magnetically attractable structure 766 of the stent 700. In act 783, the practitioner may pull the retrieving device 768 to remove both the retrieving device 768 and the stent 700.

Insertion

Measurable Guidewire Embodiments

The length of a ureter may vary depending on, for example, the age and sex of the patient. In an embodiment, at least one of the first retaining structure or the second retaining structure may include a retaining structure that enables the stent to adjust a length thereof. For example, at least one of the first retaining structure or the second retaining structure may include a curled retaining structure. Alternatively, the stent may be configured to be cut to length. However, some stents may not include retaining structures that enable the stent to adjust the length thereof and/or may contain structures that prevent the stent from being cut to length. As such, the specific length of the stent may need to be known prior to inserting the stent into the patient.

Figure 8A:
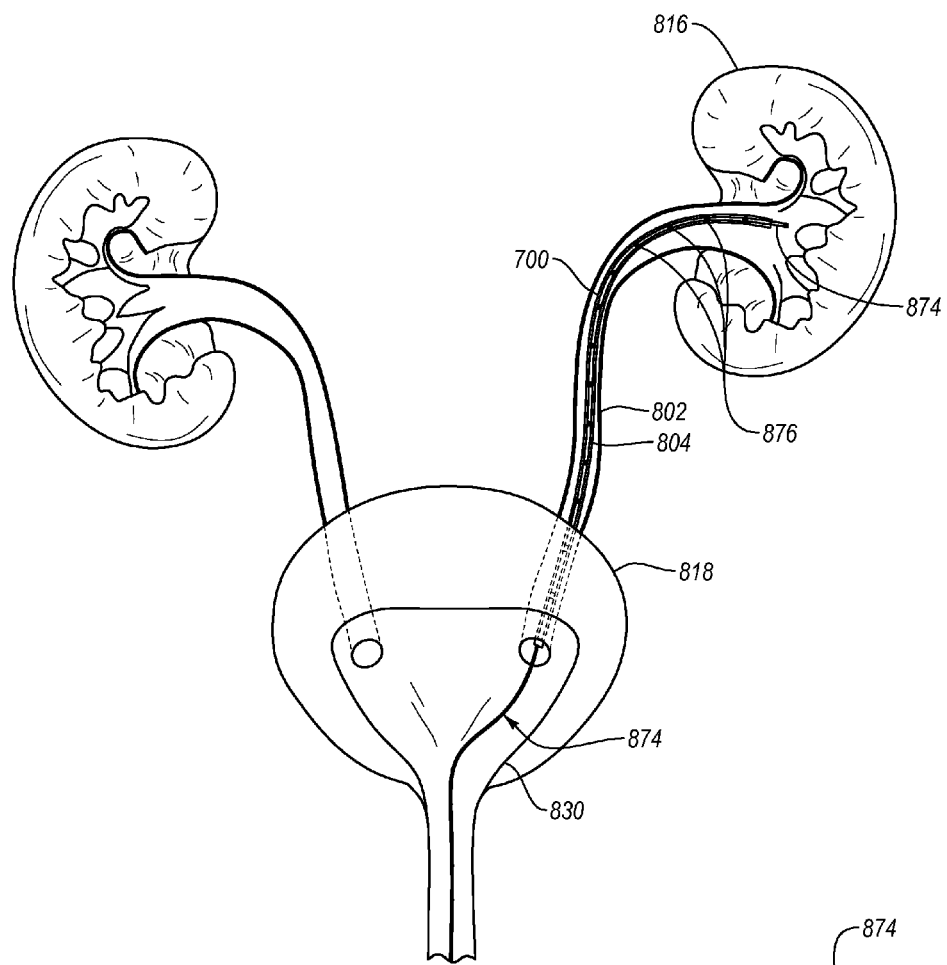
FIGS. 8A, and 8B are schematic illustrations of a guidewire that is at least partially positioned in the kidney, according to an embodiment.
Figure 8B:
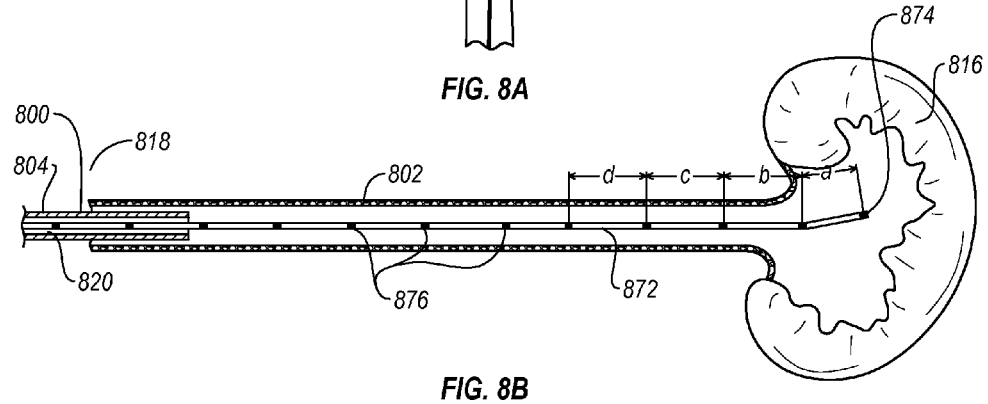

FIGS. 8A and 8B are schematic illustrations of a guidewire 872 that is at least partially positioned in the kidney 816, according to an embodiment. The guidewire 872 may include a distal tip 874 configured to be positioned in a kidney 816. In an embodiment, the guidewire 872 includes a plurality of marker structures 876, such as radiopaque marker structures. The distance between each of plurality of marker structures 876 may be known. For example, the distance "a," "b", "c", etc. may be known. In an embodiment, the distance between each of the plurality of marker structures 876 may be the same, (i.e. a=b=c). The plurality of marker structures 876 may be visualized using standard visualization techniques. For example, each of the plurality of marker structures 876 may be visualized by a practitioner using fluoroscopy or other imaging technique. As such, the practitioner may use the guidewire 872 to measure the ureter 802 (e.g., the length of the ureter 802) or ureter 802 adjacent structures (e.g., the width of a portion of the kidney 816 to receive the first end 810). The practitioner may use the measurements to select a stent 800 exhibiting an appropriate length. The stent 800 exhibiting an appropriate length may include less excessive material that may irritate a trigone 830.

In an embodiment, the stent 800 may be at least partially positioned in the ureter 802 using the guidewire 872. For example, the stent 800 may include an elongated member 704 having a structure (e.g. a lumen 820), that may receive the guidewire 872. For example, the stent 800 may be threaded onto the guidewire 872. The stent 800 may then be inserted into the patient and positioned using the guidewire 872.

Figure 8C:
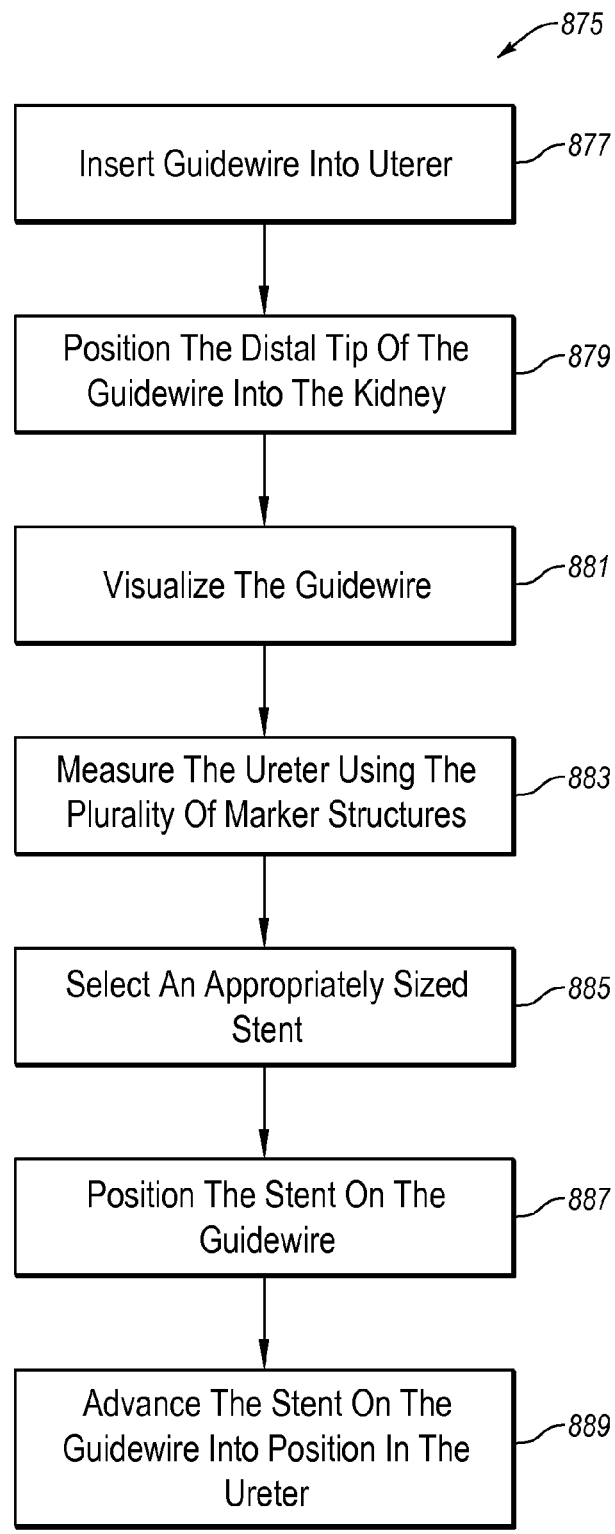
FIG. 8C is a flow diagram of a method of using a guidewire to select and position a suitably sized stent, according to an embodiment.

FIG. 8C is a flow diagram of a method 875 of using the guidewire 872, according to an embodiment. In act 877 of the method 875, a practitioner may insert the guidewire 872 into the ureter 802. For example, portions of the guidewire 872 may be inserted into the urethra 842, through bladder 818 and into the ureter 802. In act 879, the practitioner may position the distal tip 874 of the guidewire 872 into the kidney 816. The act 881, the practitioner may visualize the guidewire 872 using a standard visualization techniques. For example, the practitioner may visualize the plurality of marker structures 876 using fluoroscopy or other suitable imaging technique. In act 883, the practitioner may measure the ureter 802 using the plurality of marker structure 876. Additionally, the practitioner may measure ureter 802 adjacent structures, such as portions of the kidney 816. In act 885, the practitioner may select an appropriately sized stent at least partially based on the measurements from act 883. The practitioner may select the length using the measurements obtain in act 883. For example, the practitioner may select the stent 800 exhibiting a length sufficient to have the first end 810 positioned in the kidney 816 and the second end 812 positioned in the bladder 818. Alternatively, the practitioner may select the stent 800 exhibiting a length sufficient to have the first end 810 positioned in the kidney 816 and the second end 812 positioned in the ureter 802. In act 887, the practitioner may position the stent 800 on the guidewire 872. In act 889, the practitioner may advance the stent 800 on guidewire 872 into position in the ureter 802. After the stent 800 is positioned in the ureter 802, the practitioner may remove the guidewire 872 from the patient.

Coatings

Anti-Bacterial Coating Embodiments

Any of the embodiments disclosed herein may include a first coat applied to at least a portion of the stent. For example, one or more of the elongated member, the lumen, the first retaining structure, or the second retaining structure may have the first coating applied thereto. In an embodiment, the first coating may include anti-bacterial coating. The anti-bacterial coating may include a metal, such as gold, palladium, silver, alloys thereof, and combinations thereof. Compared to an uncoated stent, the anti-bacterial coating may reduce the likelihood of infection caused by the stent. The anti-bacterial coating may be applied to a stent configured to be used during an extended period. In an embodiment, the first coating may include ions and/or molecules to be released by the first coating into the surrounding environment. The ions and/or molecules may be configured, for example, to decrease the likelihood of infection caused by the stent. In an embodiment, the first coating may be configuring to not interfere with the operation of one or more components of the stent. For example, the first coating may be configured to not inhibit the movement of the collar structure 454 shown in FIG. 4B.

The first coating may have a second coating applied thereto. In an embodiment, the second coating may be configured to protect the first coating. For example, the second coating may include a hydrogel. In another embodiment, the second coating may transport ions or molecules from the first coating into the environment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A ureteral stent, comprising:
   an elongated member defining a drainage lumen, the elongated member including:

a first end including a first tip, a first retaining structure, and one or more openings in fluid communication with the drainage lumen, the first end for positioning in a kidney; and a second end spaced longitudinally from the first end, the second end including a second tip longitudinally spaced from the first tip, a second retaining structure, and one or more openings in fluid communication with the drainage lumen, the second retaining structure including one or more of:

a sponge structure positioned between the first tip of the first end and the second tip of the second end, the sponge structure exhibiting an outer diameter that decreases with increased proximity to the second end;

a flared structure and a collar structure, the flared structure including a proximal end and a distal end that is spaced from the proximal end, the distal end coupled to the rest of the elongated member and exhibiting an outer diameter than is substantially similar to the diameter of the rest of the elongated member, the proximal end exhibiting a maximum outer diameter that is substantially greater than the diameter of the rest of the elongated member when the flared structure is not compressed, the flared structure exhibiting a diameter that is substantially the same as a diameter of the elongated member when the flared structure is compressed, the collar structure configured to move along the elongated member, the collar structure configured to compress the flared structure; or a suture structure including at least one dissolvable suture that is dissolvable in a subject.

2. The ureteral stent of claim 1, wherein the elongated member exhibits a length such that the first end can be positioned in the kidney when the second end is positioned within a ureter.

3. The ureteral stent of claim 1, wherein the elongated member exhibits a length such that the first end can be positioned in the kidney when the second end is positioned in a bladder.

4. The ureteral stent of claim 1, wherein the elongated member is configured to substantially prevent urine reflux.

5. The ureteral stent of claim 1, wherein the sponge structure includes at least one of a sponge or a material that absorbs moisture.

6. The ureteral stent of claim 5, wherein the sponge structure exhibits a shape configured to aid in removal of the elongated member from a subject.

7. The ureteral stent of claim 1, wherein the flared structure includes at least one of one or more flaps, one or more barbs, or one or more tabs.

8. The ureteral stent of claim 1, wherein the collar structure includes a string attached thereto configured to move the collar structure along the elongated member towards the second end.

9. The ureteral stent of claim 1, wherein the first retaining structure includes a balloon structure, the balloon structure including a balloon.

10. The ureteral stent of claim 9, further comprising an inflation tube configured to conduct a fluid into the balloon structure that inflates the balloon.

11. The ureteral stent of claim 1, wherein the suture structure includes an attachment structure that allows the at least one dissolvable suture to attach to the stent.

12. The ureteral stent of claim 1, wherein the second end exhibits a weight that is greater than any other portion of the elongated member having substantially the same length.

13. The ureteral stent of claim 1, wherein the elongated member is coated with a material selected from the group consisting of gold, palladium, silver, alloys thereof, and combinations thereof.

14. The ureteral stent of claim 1, wherein the second end includes a magnetically attractable structure, wherein the magnetically attractable structure includes at least one of a magnet or a magnetically attractable material.

15. The ureteral stent of claim 1, wherein the first retaining structure and the second retaining structure are substantially the same.

16. A method of inserting a stent into a ureter, the method comprising:

inserting a distal tip of a guidewire into a bladder and up the ureter, the guidewire including a plurality of marker structures having a known length between the each of the marker structures, the plurality of marker structures configured to be visualized by a practitioner using a visualization technique;

positioning the distal tip of the guidewire into a kidney that is drained by the ureter;

visualizing the plurality marker structures using the visualizing technique; measuring a length of the ureter using the plurality of marker structures;

selecting a stent including a first end and a second end spaced longitudinally from the first end, the stent having a length selected to have a first portion of the stent positioned in the kidney and a second portion positioned in the ureter, the first portion includes the first end;

positioning the stent on the guidewire; and advancing the stent on the guidewire until the first portion of the stent is positioned in the kidney and the second portion of the stent within the ureter.

17. The method of claim 16, further comprising securing the stent in position using a first retaining structure and a second retaining structure, the first end includes the first retaining structure and the second end includes the second retaining structure, the first retaining structure configured to prevent the stent from moving towards the bladder and the second retaining structure configured to prevent the stent from moving towards the kidney.

18. The method of claim 16, wherein selecting a stent including a first end and a second end spaced longitudinally from the first end includes selecting the stent to have a length selected to have the first portion of the stent positioned in the kidney, the second portion positioned in the ureter, and a third portion positioned in the bladder, the third portion includes the second end.

19. A method of retrieving a stent positioned in a ureter, the method comprising:

providing a stent at least partially positioned in the ureter, the stent include a first end and a second end spaced longitudinally from the first end, the first end positioned at least proximate to a kidney, the first end including a first tip and the second end including a second tip that is longitudinally spaced from the first tip, the second end including a first magnetically attractable structure and a first retaining member, the first retaining member including one or more of:

a sponge structure positioned between the first tip of the first end and the second tip of the second end, the sponge structure exhibiting an outer diameter that decreases with increased proximity to the second end;

a flared structure including a proximal end and a distal end that is spaced from the proximal end, the distal end coupled to the rest of the stent and exhibiting an outer diameter that is substantially similar to a diameter of the rest of the stent, the proximate end exhibiting a maximum out diameter that is substantially greater than the diameter of the rest of the stent when the flared structure is not compressed and substantially the same as the diameter of the of the stent when the flared structure is compressed; or a suture structure including at least one dissolvable suture that is dissolvable in a subject;

inserting a distal end of a retrieval device into a bladder, the retrieval device having a second magnetically attractable structure at or near the distal end thereof;

positioning the distal end of the retrieval device at least proximate to the second end of the stent such that the first and second magnetically attractable structures are magnetically attracted to each other;

applying a pulling force to the retrieving device to retrieve the stent from the ureter; and removing the stent from the ureter by at least one of compressing the sponge structure, compressing the flared structure, or breaking the at least one dissolvable suture.

20. An ureteral stent, comprising:
an elongated member defining a drainage lumen, the elongated member including:
a first end including a first tip, a first retaining structure, and one or more openings in fluid communication with the drainage lumen, the first end for positioning in a kidney; and
a second end spaced longitudinally from the first end, the second end including a second tip longitudinally spaced from the first tip, a second retaining structure, and one or more openings in fluid communication with the drainage lumen, the second retaining structure including a sponge structure positioned between the first tip of the first end and the second tip of the second end, the sponge structure exhibiting an outer diameter that decreases with increased proximity to the second end.

21. The ureteral stent of claim 20, wherein the sponge structure includes a material that absorbs moisture.

22. The ureteral stent of claim 21, wherein the material that absorbs moisture includes a sponge.

23. The ureteral stent of claim 20, wherein the sponge structure exhibits a shape configured to aid in removal of the elongated member from a subject.

24. The ureteral stent of claim 20, wherein the sponge structure exhibits a generally conical shape when expanded.

25. An ureteral stent, comprising:
an elongated member defining a drainage lumen, the elongated member including:
a first end including a first tip, a first retaining structure, and one or more openings in fluid communication with the drainage lumen, the first end for positioning in a kidney; and
a second end spaced longitudinally from the first end, the second end including a second tip longitudinally spaced from the first tip, a second retaining structure, and one or more openings in fluid communication with the drainage lumen, the second retaining structure including:
a flared structure; and
a collar structure;
wherein the flared structure includes a proximal end and a distal end that is spaced from the proximal end, the distal end coupled to the rest of the elongated member and exhibiting an outer diameter than is substantially similar to the diameter of the rest of the elongated member, the proximal end exhibiting a maximum outer diameter that is substantially greater than the diameter of the rest of the elongated member when the flared structure is not compressed, the flared structure exhibiting a diameter that is substantially the same as a diameter of the elongated member when the flared structure is compressed by the collar structure;
wherein the collar structure is configured to move along the elongated member, the collar structure configured to compress the flared structure.

26. The ureteral stent of claim 25, wherein the flared structure includes at least one of one or more flaps, one or more barbs, or one or more tabs.

27. The ureteral stent of claim 25, wherein the collar structure includes a string attached thereto configured to move the collar structure along the elongated member towards the second end.

28. The ureteral stent of claim 25, wherein the first retaining structure includes a balloon structure, the balloon structure including a balloon.

29. The ureteral stent of claim 28, further comprising an inflation tube configured to conduct a fluid into the balloon structure that inflates the balloon.

30. The ureteral stent of claim 25, wherein the first retaining structure and the second retaining structure are substantially the same.

* * * * *